US00PP33804P2

(12) United States Plant Patent
Mathey

(10) Patent No.: US PP33,804 P2
(45) Date of Patent: Jan. 4, 2022

(54) ***ITEA* PLANT NAMED 'SMIHGRS'**

(50) Latin Name: *Itea virginiana*
Varietal Denomination: SMIHGRS

(71) Applicant: Megan M. Mathey, Holland, MI (US)

(72) Inventor: Megan M. Mathey, Holland, MI (US)

(73) Assignee: SPRING MEADOW NURSERY INC., Grand Haven, MI (US)

( * ) Notice: Subject to any disclaimer, the term of this patent is extended or adjusted under 35 U.S.C. 154(b) by 18 days.

(21) Appl. No.: 17/121,453

(22) Filed: Dec. 14, 2020

(51) Int. Cl.
*A01H 5/00* (2018.01)

(52) U.S. Cl.
USPC ..... Plt./226

(58) Field of Classification Search
USPC ..... Plt./226
See application file for complete search history.

*Primary Examiner* — Annette H Para
(74) *Attorney, Agent, or Firm* — C. Anne Whealy

(57) ABSTRACT

A new and distinct cultivar of *Itea* plant named 'SMIHGRS', characterized by its relatively compact, upright to outwardly spreading plant habit; moderately vigorous growth habit; strong lateral branches; freely branching habit, dense and bushy appearance; green-colored leaves that become dark red in color during the autumn; freely flowering habit with numerous white-colored flowers on relatively long racemes; and good garden performance.

3 Drawing Sheets

Figure 1:
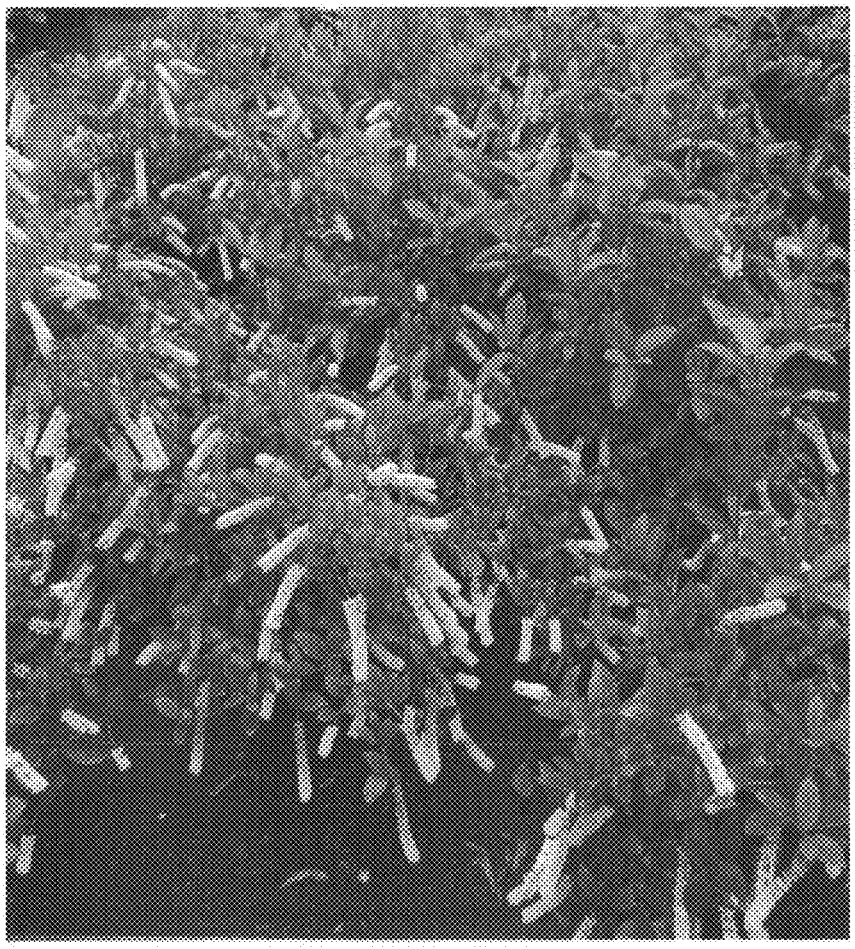

Botanical designation: *Itea virginiana.*
Cultivar denomination: 'SMIHGRS'.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct *Itea* plant, botanically known as *Itea virginiana*, commonly referred to as Virginia Sweetspire and hereinafter referred to by the name 'SMIHGRS'.

The new *Itea* plant is a product of a planned breeding program conducted by the Inventor in Grand Haven, Mich. The objective of the breeding program was to create new compact and freely-branching *Itea* plants with large inflorescences with attractive flowers and attractive autumn leaf coloration.

The new *Itea* plant originated from an open-pollination during the spring of 2014 in Grand Haven, Mich. of *Itea virginiana* 'Henry's Garnet', not patented, as the female, or seed, parent with an unknown proprietary selection of *Itea virginiana* as the male, or pollen, parent. The new *Itea* plant was discovered and selected by the Inventor as a single plant within the progeny of the stated open-pollination in a controlled environment in Grand Haven, Mich. during the spring of 2016.

Asexual reproduction of the new *Itea* plant by softwood stem cuttings in a controlled environment in Grand Haven, Mich. since the spring of 2016 has shown that the unique features of this new *Itea* plant are stable and reproduced true to type in successive generations.

SUMMARY OF THE INVENTION

Plants of the new *Itea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMIHGRS'. These characteristics in combination distinguish 'SMIHGRS' as a new and distinct *Itea* plant:

1. Relatively compact, upright to outwardly spreading plant habit.
2. Moderately vigorous growth habit.
3. Strong lateral branches.
4. Freely branching habit, dense and bushy appearance.
5. Green-colored leaves that become dark red in color during the autumn.
6. Freely flowering habit with numerous white-colored flowers on relatively long racemes.
7. Good garden performance.

Plants of the new *Itea* differ primarily from plants of the female parent, 'Henry's Garnet', in the following characteristics:

1. During the spring and summer, leaves of plants of the new *Itea* are lighter green in color than leaves of plants of 'Henry's Garnet'.
2. During the autumn, leaves of plants of the new *Itea* are darker red in color than leaves of plants of 'Henry's Garnet'.

3. Plants of the new *Itea* have longer inflorescences than plants of 'Henry's Garnet'.

Plants of the new *Itea* can be compared to plants of *Itea virginiana* 'Sprich', disclosed in U.S. Plant Pat. No. 10,988. In side-by-side comparisons, plants of the new *Itea* differ primarily from plants of 'Sprich' in autumnal leaf color as leaves of plants of the new *Itea* become dark red in color during the autumn whereas leaves of plants of 'Sprich' become lighter red in color during the autumn.

BRIEF DESCRIPTION OF THE PHOTOGRAPHS

The accompanying colored photographs illustrate the overall appearance of the new *Itea* plant showing the colors as true as it is reasonably possible to obtain in colored reproductions of this type. Colors in the photographs may differ slightly from the color values cited in the detailed botanical description which accurately describe the colors of the new *Itea* plant.

The photograph on the first sheet (FIG. 1) is a side perspective view of typical flowering plants of 'SMIHGRS' grown during the summer.

Figure 2:
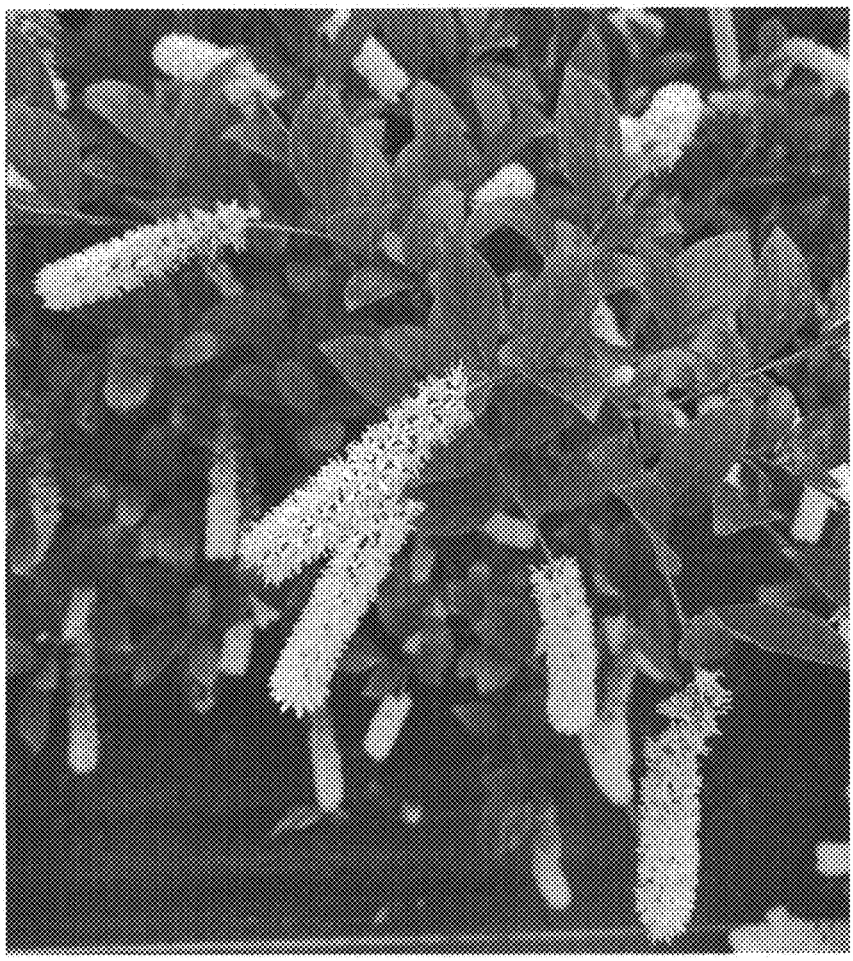

The photograph on the second sheet (FIG. 2) is a close-up view of typical inflorescences and leaves of 'SMIHGRS'.

Figure 3:
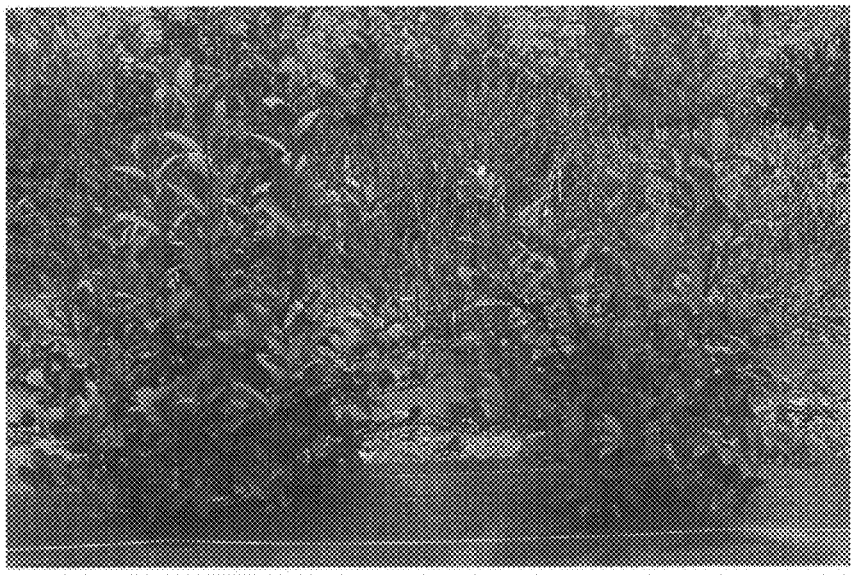

The photograph on the third sheet (FIG. 3) is a side perspective view of typical plants of 'SMIHGRS' grown during the autumn in an outdoor nursery.

DETAILED BOTANICAL DESCRIPTION

The aforementioned photographs and following observations, measurements and values describe plants grown during the spring, summer and autumn in three-gallon containers in a polyethylene-covered greenhouse in Grand Haven, Mich. and under cultural practices typical of commercial production. Plants were two years old when the photographs and description were taken. During the production of the plants, day temperatures ranged from 18° C. to 27° C. and night temperatures ranged from 5° C. to 10° C. In the following description, color references are made to The Royal Horticultural Society Colour Chart, 2015 Edition, except where general terms of ordinary dictionary significance are used.

Botanical classification: *Itea virginiana* 'SMIHGRS'.

Parentage:

*Female, or seed, parent.*—*Itea virginiana* 'Henry's Garnet', not patented.

*Male, or pollen, parent.*—Unknown proprietary selection of *Itea virginiana*, not patented.

Propagation:

*Type.*—By softwood stem cuttings.

*Time to initiate roots plant, summer.*—About three to four weeks at temperatures ranging from 18° C. to 27° C.

*Time to produce a rooted plant, summer.*—About three months at temperatures ranging from 18° C. to 27° C.

*Root description.*—Fine, fibrous; typically white in color, actual color of the roots is dependent on substrate composition, water quality, fertilizer, substrate temperature and physiological age of roots.

*Rooting habit.*—Freely branching; medium density.

Plant description:

*Plant and growth habit.*—Deciduous perennial shrub; relatively compact, upright and outwardly spreading plant habit; dense and bushy appearance; moderately vigorous growth habit and rapid growth rate.

*Plant height.*—About 58 cm.

*Plant width (spread).*—About 71 cm.

*Lateral branches.*—Quantity: Freely branching habit with about 20 primary lateral branches developing per plant; pinching enhances lateral branch development. Length: About 41 cm. Diameter: About 4 mm. Internode length: About 1.5 cm. Strength: Strong. Aspect: Erect to about 90° from vertical. Texture: Smooth, glabrous. Color: Close to 138A variably tinged with close to 187A.

Leaf description:

*Arrangement.*—Alternate, simple.

*Length.*—About 7.25 cm.

*Width.*—About 3.5 cm.

*Shape.*—Elliptical.

*Apex.*—Acute.

*Base.*—Attenuate.

*Margin.*—Serrate.

*Texture, upper surface.*—Smooth, glabrous.

*Texture, lower surface.*—Slightly rough with prominent venation, glabrous.

*Venation pattern.*—Pinnate.

*Color, developing leaves, upper surface.*—Spring and summer: Close to 143A; towards the apex and margins, variably tinged with close to 180A. Autumn: Close to 187B to 187C.

*Color, developing leaves, lower surface.*—Spring and summer: Close to 144A. Autumn: Close to 191A.

*Color, fully expanded leaves, upper surface.*—Spring and summer: Close to 143A; venation, close to 175D. Autumn: Close to N186C; occasionally with close to 191A and 197B to 197C; venation, similar to lamina

*Color, fully expanded leaves, lower surface.*—Spring and summer: Close to 143C; venation, close to 185C. Autumn: Close to 191A and 187C; or, occasionally, close to 163D; venation, similar to lamina

*Petioles.*—Length: About 1 cm. Diameter: About 1.5 mm. Texture, upper and lower surfaces: Slightly pubescent. Color, upper surface: Close to 187C. Color, lower surface: Close to 185B.

Flower description:

*Flower type and flowering habit.*—Single broad star-shaped flowers arranged on terminal and axillary racemes; racemes narrowly conical in shape and relatively long; racemes may be upright, arching outwardly or drooping; freely flowering habit with more than 100 flowers developing per inflorescence and numerous inflorescences developing per plant during the flowering season; flowers face mostly outwardly depending on the position on the inflorescence; flowers persistent.

*Fragrance.*—Fragrant, slightly earthy; pleasant.

*Natural flowering season.*—Plants flower continuously from the late spring into the summer in Michigan.

*Flower buds.*—Height: About 4 mm. Diameter: About 2 mm. Shape: Ovoid. Color: Close to 157B.

*Inflorescence length.*—About 5 cm.

*Inflorescence diameter.*—About 2.5 cm.

*Flower diameter.*—About 1 cm.

*Flower depth.*—About 4 mm.

*Petals.*—Quantity per flower: Typically five in a single whorl. Length: About 5 mm. Width: About 1 mm.

Shape: Acicular. Apex: Acute. Base: Truncate. Margin: Entire. Texture, upper and lower surfaces: Smooth, glabrous; delicate. Color: Developing petals, upper and lower surfaces: Close to NN155D. Fully developed petals, upper and lower surfaces: Close to NN155D; color becoming closer to 199A with development.

*Sepals*.—Calyx length: About 2 mm. Calyx diameter: About 2 mm. Quantity and arrangement: Inconspicuous; typically five sepals per flower arranged in a single whorl. Length: About 2 mm. Diameter: About 0.5 mm. Shape: Narrowly deltoid. Apex: Acute. Base: Truncate. Margin: Entire. Texture, upper and lower surfaces: Smooth, glabrous. Color, upper and lower surfaces: Close to 160C.

*Peduncles*.—Length: About 2.5 cm. Diameter: About 2 mm. Strength: Strong, flexible. Angle: Upright to outwardly. Texture: Slightly pubescent. Color: Close to 144A.

*Pedicels*.—Length: About 2 mm. Diameter: About 1 mm. Strength: Strong, flexible. Angle: About 45° from peduncle axis. Texture: Smooth, glabrous. Color: Close to 144A.

*Reproductive organs*.—Stamens: Quantity per flower: Typically five. Filament length: About 2 mm. Filament color: Close to NN155D. Anther length: Less than 1 mm. Anther shape: Globular. Anther color: Close to NN155D. Pollen amount: Moderate. Pollen color: Close to NN155D. Pistils: Quantity per flower: One. Pistil length: About 1.5 mm. Style length: Less than 1 mm. Style color: Close to NN155D. Stigma shape: Rounded. Stigma color: Close to NN155D.

*Seeds and fruits*.—To date, seed and fruit development have not been observed on plants of the new *Itea*.

Pathogen & pest resistance: To date, plants of the new *Itea* have not been observed to be resistant to pathogens and pests common to *Itea* plants.

Garden performance: Plants of the new *Itea* have been observed to have good garden performance and tolerate rain, wind and to tolerate temperatures ranging from about −32° C. to about 36° C.

It is claimed:

1. A new and distinct *Itea* plant named 'SMIHGRS' as illustrated and described.

* * * * *